United States Patent
Li et al.

(10) Patent No.: US 10,507,216 B2
(45) Date of Patent: Dec. 17, 2019

(54) METHOD FOR OLFACTORY IMPROVEMENT WITH SACCHARIDE

(71) Applicant: Tsung-Wei Huang, New Taipei (TW)

(72) Inventors: Sheng-Tien Li, Tainan (TW);
Tsung-Wei Huang, New Taipei (TW);
Li-Ping Yang, Taipei (TW)

(73) Assignee: Tsung-Wei Huang, New Taipei (TW)

( * ) Notice: Subject to any disclaimer, the term of this patent is extended or adjusted under 35 U.S.C. 154(b) by 11 days.

(21) Appl. No.: 15/943,400

(22) Filed: Apr. 2, 2018

(65) Prior Publication Data

US 2019/0099440 A1    Apr. 4, 2019

(30) Foreign Application Priority Data

Oct. 3, 2017  (TW) .............................. 106134150 A

(51) Int. Cl.

| | | |
|---|---|---|
| *A61K 31/722* | (2006.01) | |
| *A61K 31/727* | (2006.01) | |
| *A61K 31/728* | (2006.01) | |
| *A61K 9/00* | (2006.01) | |
| *A61K 31/7008* | (2006.01) | |
| *A61P 27/00* | (2006.01) | |

(52) U.S. Cl.
CPC .......... *A61K 31/722* (2013.01); *A61K 9/0043* (2013.01); *A61K 31/7008* (2013.01); *A61K 31/727* (2013.01); *A61K 31/728* (2013.01); *A61P 27/00* (2018.01); *A61K 2300/00* (2013.01)

(58) Field of Classification Search
None
See application file for complete search history.

(56) References Cited

U.S. PATENT DOCUMENTS

2002/0068080 A1 *  6/2002  Lerner .................. A61K 9/0009
                                                  424/434
2013/0210761 A1 *  8/2013  Baker .................. A61K 31/722
                                                  514/54

OTHER PUBLICATIONS

Ciofalo, Eur Arch Otorhinolaryngol (2017) 274:803-808, published Aug. 27, 2016. (Year: 2016).*
Ciofalo et al., "Olfactory dysfunction in acute rhinosinusitis: intranasal sodium hyaluronate as adjuvant treatment," Eur Arch Otorhinolaryingol, 2017, pp. 803-808.
Sheng-Tien Li, et al, "The effect of chitosan on rat olfactory neuroepithelium cells," Proceedings of the 2nd World Congress on Recent Advances in Nanotechnology (RAN'17), Apr. 5-6, 2017, 1 page, Barcelona, Spain.
Sheng-Tien Li, et al, "Promotion of olfactory receptor neuron differentiation of olfactory neuroepithelial cells by using chitosan solution," American Journal of Rhinology & Allergy, vol. 31, 2017, pp. 289-292.

* cited by examiner

*Primary Examiner* — Layla D Berry
(74) *Attorney, Agent, or Firm* — Muncy, Geissler, Olds & Lowe, P.C.

(57) ABSTRACT

A method for olfactory improvement with saccharide. The saccharide is a chitin-based material, proteoglycan, glycosaminoglycan, amino monosaccharide, N-acylated amino monosaccharide or a combination thereof.

14 Claims, 16 Drawing Sheets
(4 of 16 Drawing Sheet(s) Filed in Color)

METHOD FOR OLFACTORY IMPROVEMENT WITH SACCHARIDE

CROSS REFERENCE TO RELATED APPLICATIONS

This application claims the benefits of the Taiwan Patent Application Serial Number 106134150, filed on Oct. 3, 2017, the subject matter of which is incorporated herein by reference.

FIELD OF THE INVENTION

The present invention relates to a method for olfactory improvement with saccharide.

DESCRIPTION OF RELATED ART

According to studies in different countries, the incidence of olfactory dysfunction in the general population is estimated to be about 15%. Olfactory dysfunction significantly influences patients' life quality, inclusive of taste, appetite and even an ability to identify nearby environmental hazards. As olfactory dysfunction would not immediately result in death, it is easily ignored.

Olfactory malfunction is commonly attributed to aging, viral infection of upper respiratory tract and head trauma. Among these, the first two mainly result from the number and degree of differentiation of olfactory receptor neurons (ORNs). Although promising findings have been achieved in many approaches, such as use of vitamin A, minerals and steroids, these are still inadequate in clinical treatment. Unlike other neurons, the mammalian olfactory system has a unique ability to replace ORNs continuously as the result of normal turnover or injury. The new therapeutic strategy is transplantation and engraftment of stem cells in damaged olfactory neuroepithelium (ON). The ON regeneration can be achieved by using autologous olfactory stem and progenitor cells to repair damage and alleviate the consequent dysfunction. However, the transplantation and engraftment of stem cells for treating olfactory malfunction have not been fully developed yet, and there are still big challenges in the new therapeutic strategy.

At present, there is no effective treatment for olfactory disorder, so it is desirable to develop an ingredient incredibly effective in treatment of olfactory dysfunction for improvement of olfactory function.

SUMMARY OF THE INVENTION

An objective of the present invention is to improve olfactory function of a subject by using an effective ingredient for promoting differentiation of the olfactory receptor neurons (ORNs), replacing commonly conventional therapy, for example, vitamin, minerals and steroids.

In accordance with the foregoing and other objectives, the present invention provides a method of improving olfactory function, which includes: administering an effective amount of saccharide and optionally an effective amount of neuropeptide Y (NPY) to a subject in need, wherein the saccharide is a chitin-based material, proteoglycan, glycosaminoglycan, amino monosaccharide, N-acylated amino monosaccharide or a combination thereof.

Accordingly, this invention provides a medicament for improvement of olfactory function, including an effective amount of the aforementioned saccharide and optionally an effective amount of neuropeptide Y. The medicament may further include one or more pharmaceutically or physiologically acceptable carriers, diluents, excipients or the like. The medicament is not limited to any particular delivery or formulation, but preferably is formulated into a solution form. Accordingly, the aforementioned saccharide and optional NPY can be delivered to a subject suffering from olfactory disorder via intranasal topical administration. For instance, the medicament may be formulated into a nasal dosage form (such as a nasal spray) for intranasal delivery. As a result, the saccharide and optional NPY in the medicament can adhere to nasal mucosa, and exhibit its pharmaceutical effects. Additionally, the medicament may further include one or more other active ingredients in combination with the aforementioned saccharide and optional NPY to achieve desired effects.

In the present invention, the examples of the chitin-based material include chitosan, chitosan oligosaccharide and water-soluble derivatives, but are not limited to the above. The present invention has demonstrated that chitosan can facilitate regeneration of the olfactory neuroepithelium, differentiation of ORNs and expression of signal transduction apparatuses, and thus can be used as an effective ingredient for restoration of olfactory function and treatment of olfactory dysfunction. In the present invention, the chitosan is not limited to particular molecular weight and acetylation degree, and all chitosans with different molecular weights and different acetylation degrees can be used for olfactory treatment. The "acetylation degree" refers to the mole fraction of GlcNAc groups contained in the chitosan molecule. The commercially available chitosan typically has an acetylation degree of 5% to 30%. As the solubility of chitosan in a solution depends on the acetylation degree and pH value, the chitosan can be stably dissolved in aqueous medium by selecting chitosan with appropriate acetylation degree and adjusting pH value in the preparation of the chitosan solution. For instance, in a preferred embodiment of the present invention, chitosan with deacetylation degree of 75% or more is used to prepare an aqueous solution of about pH 7.2. Alternatively, chitosan oligosaccharide with lower molecular weight (such as chitobiose, chitotriose, chitotetraose, chitinpentaose or chitohexaose) or other water-soluble chitosan derivatives may be used for higher solubility. Additionally, the present invention further reveals that proteoglycan, glycosaminoglycan and their monomers (i.e. amino monosaccharide, N-acylated amino monosaccharide) also exhibit the aforementioned effects, and thus can be used as effective ingredients for treating olfactory dysfunction. The proteoglycan, glycosaminoglycan, amino monosaccharide and N-acylated amino monosaccharide of the present invention are not limited to heparan sulfate proteoglycan (HSPG), hyaluronic acid (HA), N-acetylglucosamine (GlcNAc), N-acetylgalactosamine (GalNAc), N-acetyl-D-mannosamine (ManNAc) and glucosamine (GlcN), mentioned in the following embodiments. Further, this invention has demonstrated that the saccharide can be combined with neuropeptide Y to show synergistic effect on the improvement of olfactory function. For instance, in a preferred embodiment of the present invention, the combination of chitosan and neuropeptide Y is significantly effective in promoting the maturation of ORNs.

In the present invention, the medicament is suitable for a subject (such as human) suffered from olfactory dysfunction. For instance, the medicament may be administrated to subjects with hyposmia or anosmia caused by degeneration of olfactory neuroepithelium so as to improve olfactory function. Compared to the conventional therapeutic strategy with topical steroids or systemic corticosteroids, the saccharide in the medicament as an active ingredient is effective in the treatment of olfactory malfunction with reduced side effects. Additionally, the present invention further reveals that the aforementioned saccharide can also be used in the preparation of a medicament for facilitating regeneration of respiratory epithelium and olfactory neuroepithelium. As a result, the aforementioned saccharide not only improves olfactory function, but also promotes regeneration of respiratory epithelium and ciliogenesis. For instance, in a preferred embodiment of the present invention, the combination of chitosan and HA is effective in facilitating regeneration of respiratory epithelium and olfactory neuroepithelium. Accordingly, the aforementioned saccharide of the present invention can be formulated into a nasal spray for healthcare after surgical treatment of nasal diseases.

The "effective amount" as used herein refers to the essential amount of the active agent in the medicament for sufficiently reaching the desired medical or pharmaceutical effects. The effective amount may be determined by considering various factors, such as the severity of the disease, the patient's response, the administration routes, therapy, the co-administered drugs or other relevant conditions. For instance, the effective amount of the saccharide in the medicament may be 0.001 wt % or more, preferably 0.005 wt % to 1.5 wt % and more preferably 0.005 wt % to 1 wt %, whereas the effective amount of the NPY in the medicament may be $5 \times 10^{-8}$ wt % or more and preferably $5 \times 10^{-8}$ wt % to $10 \times 10^{-8}$ wt %.

The "chitin-based material" as used herein refers to polysaccharides/oligosaccharides containing N-acetyl-glucosamine or/and glucosamine as monomers and their derivatives. The "derivative" as used herein refers to a different compound modified from its "parent" compound by replacing one or more atoms or groups of the "parent" compound with other different atoms or groups, for example. A derivative typically exhibits an overall biological effect similar to that of the "parent" compound, but may differ in one or more physicochemical and/or pharmacokinetic properties (such as potency, stability, solubility, absorption, in vivo half-life, etc.). For instance, the "water-soluble derivative" as used herein refers to derivatives with a structure, similar to its parent compound and higher water-solubility. More specifically, in addition to chitosan oligosaccharide, many other modified chitosans with higher water-solubility (i.e. water-soluble chitosan derivatives) have been developed. The examples of water-soluble chitosan derivatives include chitosan hydrochloride, chitosan acetate, chitosan lactate, carboxymethyl chitosan, hydroxypropyl chitosan and the like, but are not limited to the above.

The "amino monosaccharide" as used herein refers to a monosaccharide in which one hydroxyl group (—OH) is replaced by an amino group (—NH$_2$), such as six-membered cyclic monosaccharide (i.e. pyranose monosaccharide) with an amino group on C-2 carbon.

The "N-acylated amino monosaccharide" as used herein refers to an amino monosaccharide in which the amino group (—NH$_2$) is acylated, namely, a monosaccharide in which one hydroxyl group (—OH) is replaced by —NHC(O)R, such as six-membered cyclic monosaccharide (i.e. pyranose monosaccharide) with a —NHC(O)R group on C-2 carbon, wherein R is hydrogen or alkyl group (such as $C_1$-$C_8$ alkyl group, including methyl, ethyl, propyl, etc.). Accordingly, the "N-acylated amino monosaccharide" may be N-formylated amino monosaccharide, N-acetylated amino monosaccharide, N-propionylated amino monosaccharide and so on.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

«Materials and Methods»

Rat Olfactory Neuroepithelial Cells (ONCs)

Figure 1:
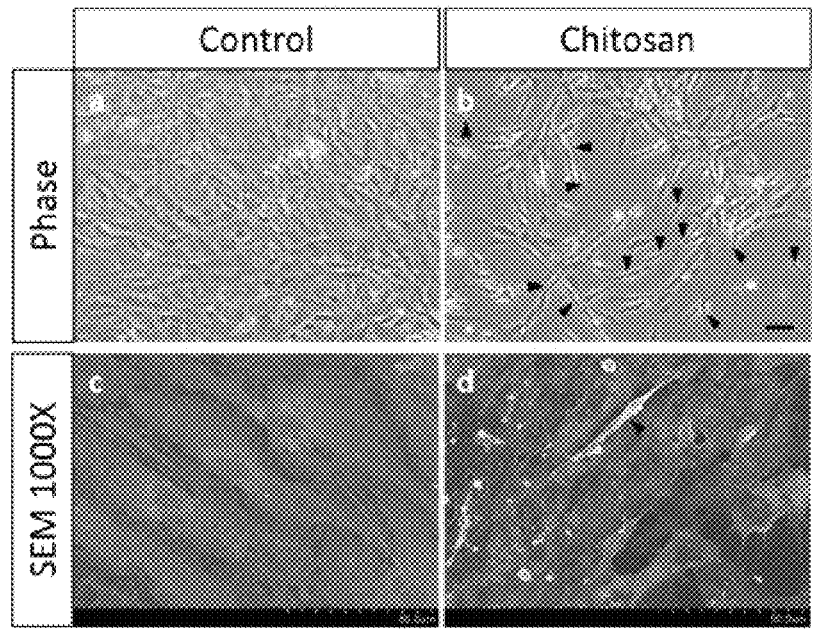
FIG. 1 shows the morphology of rat ONCs in control groups and chitosan-treated groups (with 0.1 mg/ml chitosan) at day 9 assessed by phase contrast (the upper row) and scanning electron microscope (the lower row, magnification ×1000) (scale bar=50 μm)

Olfactory neuroepithelia of rats were isolated from E17 embryos of wistar rats and 40 embryos per trial were used. After isolation, olfactory neuroepithelia were digested in Hanks' balanced salt solution (Roche Molecular Biochemicals, Indianapolis, Ind., USA) containing 0.125% Trypsin/EDTA for 30 minutes at 37° C. The cell suspension was then filtered through a 70 μm cell strainer to eliminate cell aggregates and debris, and adjusted to $24 \times 10^4$ cells/mL (equivalent to $5 \times 10^4$ cells/cm$^2$). Finally, a 2 mL cell suspension was added to six-wells coated with 0.85 μg/cm$^2$ poly-L-lysine (PLL). ONCs were cultured at 37° C. in a humidified 5% $CO_2$ and 95% air atmosphere. Cell morphology was observed under an inverse phase contrast microscope (TS-100, Nikon, Tokyo, Japan) and scanning electron microscope (Hitachi S-4800).

ONC medium comprised DMEM/F12 (Invitrogen), 20 ng/mL bFGF, 20 ng/mL EGF, 2% B27 and 1% penicillin/streptomycin. To prepare the chitosan-containing medium for administration groups, chitosan (C-3646, Sigma, St. Louis, Mo.) was mixed with culture medium (0.1 mg/mL), and adjusted to pH 7.2 with NaOH. Particularly, chitosan solution was prepared by dissolving chitosan in 0.5 M acetic acid. Hence, mock culture medium for control groups was prepared similarly to chitosan-containing ONC medium, mixing the same amount of acetic acid and NaOH without adding chitosan.

Human Olfactory Neuroepithelial Cells (ONCs)

Human olfactory neuroepithelia were harvested from adult olfactory neuroepithelium during endoscopic sinus surgery. Biopsy specimens were transferred into Hank's balanced salt solution (HBSS), minced finely, and then digested with 0.125% Trypsin/EDTA for 30 minutes at 37° C. After digestion, the pellet was collected by centrifuge and resuspended in the iscove's modified dulbecco's media (IMDM; Invitrogen, Calif., USA) with 10% fetal bovine serum and 1% penicillin/streptomycin Finally, they were seeded to six-wells coated with laminin-co-fibronectin for 21 days, incubated in a humidified atmosphere containing 5% $CO_2$ and 95% air. After 21 days, the medium were changed with induction medium. This induction medium is Dulbecco's Modified Eagle Medium: Nutrient Mixture F-12 (DMEM/F12) (Invitrogen, Calif., USA) supplemented with 2% B-27 serum-free supplement. To prepare the chitosan-containing medium for administration groups, chitosan (C-3646, Sigma-Aldrich, St. Louis, Mo.) was mixed with induction medium (0.1 mg/ml), and adjusted to pH 7.2 with NaOH. Hence, mock induction medium for control groups was prepared similarly to chitosan-containing medium, mixing the same amount of acetic acid and NaOH without adding chitosan.

Human Respiratory Epithelium Cells (RECs)

Human nasal inferior turbinates were obtained from patients undergoing septomeatoplasty. Tissues were treated with 0.5% Pronase (type XIV protease, Sigma-Aldrich, St Louis, Mo., USA) in a 1:1 mixture of Dulbecco's modified Eagle's medium and Ham's nutrient F12 (DMEM/F12) supplemented with antibiotics (i.e. penicillin/streptomycin) for 16 to 20 hours at 4° C. The cell suspension was filtered through a 40 μm cell strainer to remove cell aggregates and debris. After centrifugation, the cells were suspended in DMEM/F12: bronchial epithelial growth medium (BEGM, Clonetics Corp., San Diego, Calif., USA) (1:1) supplemented with antibiotics. Next, 0.75 ml cell suspension was seeded on Transwell inserts, respectively, with 2.6 ml of the medium deposited on the basolateral side. Cultures were maintained at 37° C. in an atmosphere of 5% carbon dioxide in air. Cells were grown submerged before confluence and the culture medium was changed after 48 h first and every other day thereafter. Following confluence, an air-liquid interface (ALI) was created by removing the apical medium and feeding the cultures only from the basolateral compartment. In comparison groups treated with inflammation factors, 0.5 ng/ml TGF-β1 were added to the culture medium during ALI culture to initiate inflammation. As for administration groups, 0.1 mg/ml (about 0.01 wt %) chitosan plus 2 mg/ml (about 0.2 wt %) HA were added to the culture medium, and the culture medium was changed every day.

Immunocytochemistry

The cultured cells were fixed in 4% paraformaldehyde, and permeabilized with 0.1% Triton X-100 for 5 min at room temperature. Then, the cells were blocked in 3% bovine serum albumin (BSA) for 20 min, and incubated with primary antibodies diluted in 3% BSA overnight. The primary antibodies and their dilution utilized were used in this study: anti-βIII tubulin (Abcam, Ab118627; 1:1000), anti-olfactory marker protein (OMP) (Abcam, ab62144, 1:100), anti-olfactory marker protein (OMP) (Novus, NB110-74751, 1:100), anti-olfactory neuron specific-G protein ($G_{olf}$) (GeneTex, GTX110520; 1:100), anti-adenylate cyclase type 3 (ADCY3) (Abcam, Ab125093; 1:1000) and anti-acetyl-tubulin (Sigma-Aldrich). Green Dylight488-, red Alexa Fluor 555- or green Alexa488-conjugated secondary antibodies were adopted to visualize the signal by reacting with cells for 1.5 hours at room temperature. Additionally, blue DAPI (4',6-diamidino-2-phenylindole) and red rhodamine conjugated phalloidin were used to counterstain nuclear and cytoskeletal markers (F-actin), respectively. These immunostained cells were visualized using indirect fluorescence under a confocal microscope (LSM510, Zeiss, Germany).

Western Blot Analysis

ONC lysates were obtained from individual culture wells using a RIPA lysis buffer containing protease inhibitor cocktail tablets (Roche Diagnostics GmbH). These samples were then denatured and separated by 12% SDS-PAGE gels, and blotted onto PVDF membranes (Millipore). After blocking in a CIS blocking buffer at room temperature for 60 seconds, the membranes were probed with various primary antibodies at 4° C. overnight. Membranes were incubated with horseradish peroxidase-conjugated secondary antibodies for 1.5 hours, and finally visualized using enhanced chemiluminescence (ECL; Millipore, Billerica, Mass.). After detachment of previous primary antibodies, the membranes were also probed with GAPDH antibodies, which served as an internal control. Images of western blotting were acquired by UVP BioSpectrum 810, and analyzed by Vision Works LS software (UVP, California, USA).

Statistical Analysis

All the measurements were presented as mean±SD. Statistical significance was computed with one-way ANOVA followed by LSD test with $p<0.05$. All statistical analyses were conducted using Sigma plot v12.5.

Results

<Immunocytochemical and Morphological Characterization of Rat ONCs>

Primary rat ONCs were obtained from E17 embryos of wistar rats. During the cultural period, ONCs successfully adhered to the substrate in both chitosan and control groups at day 3. In contrast to irregular and flattened cells observed in the control groups (FIG. 1a), ONCs treated with chitosan exhibited bipolar with asymmetric processes (as indicated by arrows in FIG. 1b). Further, comparing SEM images of control groups (FIG. 1c) and chitosan groups (FIG. 1d), it was confirmed that there were bipolar cells in chitosan groups (as indicated by arrows in FIG. 1d).

<Expressions of ORNs in Rat ONCs>

Figure 2:
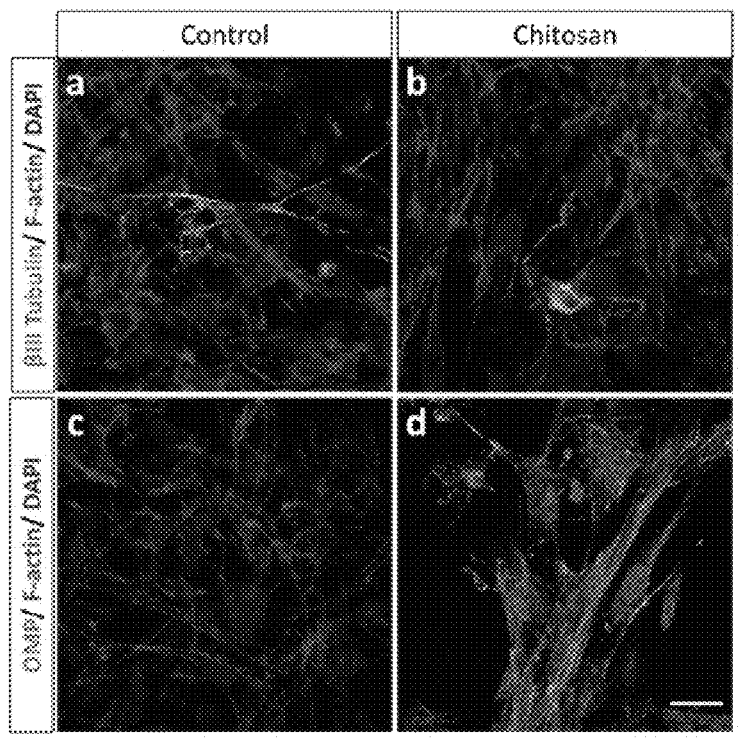
FIG. 2 shows immunofluorescence images of rat ONCs in control groups and chitosan-treated groups (with 0.1 mg/ml chitosan) at day 9 labeled by βIII tubulin (identified with green Dylight488) and OMP (identified with green Dylight488) (scale bar=20 μm)
Figure 3:
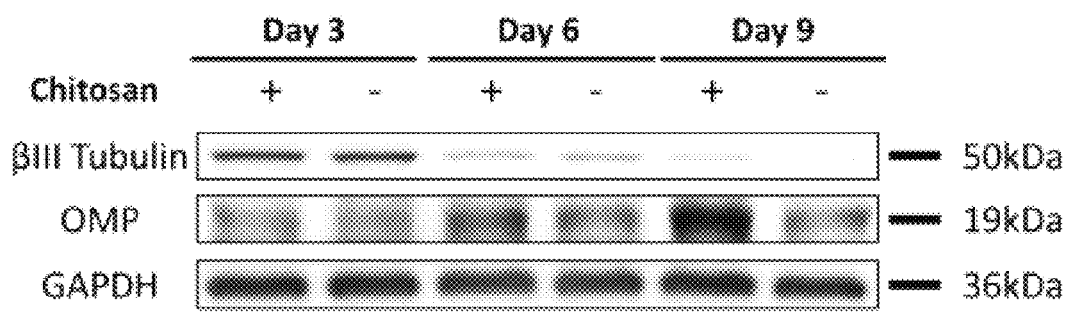
FIG. 3 shows the Western blot analysis for βIII tubulin and OMP of rat ONCs in control groups and chitosan-treated groups (with 0.1 mg/ml chitosan) from day 3 to day 9.
Figure 4:
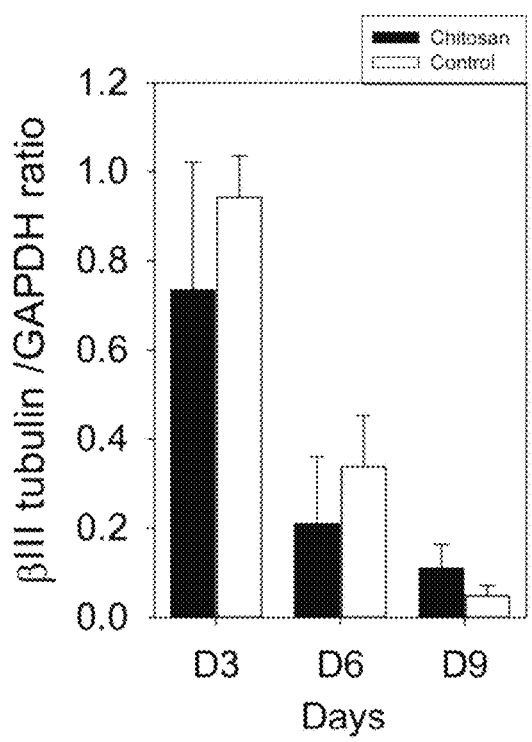
FIG. 4 shows the semi-quantitative analysis of Western blot for βIII tubulin/GAPDH of rat ONCs in control groups and chitosan-treated groups (with 0.1 mg/ml chitosan) from day 3 to day 9, in which bar charts show mean±SD of five samples.
Figure 5:
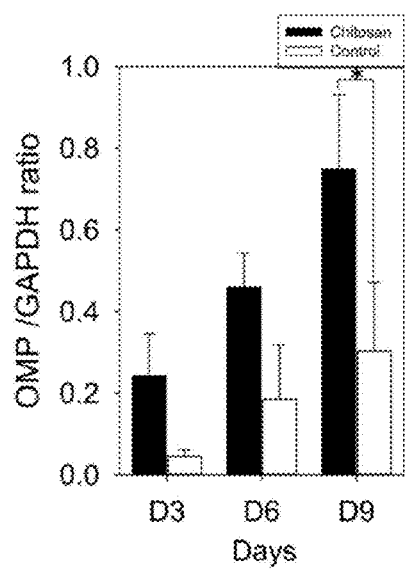
FIG. 5 shows the semi-quantitative analysis of Western blot for OMP/GAPDH of rat ONCs in control groups and chitosan-treated groups (with 0.1 mg/ml chitosan) from day 3 to day 9, in which bar charts show mean±SD of five samples; *$p<0.05$.

OMP is a representative marker of mature ORNs, while βIII tubulin is a widely accepted as indicating immature ORNs. The immunofluorescence analyzed at day 9 revealed numerous βIII tubulin-positive cells with slender and long processes located in the cytoplasm and cytoskeleton (FIGS. 2a and 2b). In contrast to no OMP-immunoreactivity in control groups, individual ORNs displayed intense OMP-immunoreactivity located in cytoplasm in the chitosan groups (FIG. 2d). The western blotting assay further confirmed these expression patterns. From days 3 to 9, the expression level of βIII tubulin gradually reduced, but the expression level of OMP rose in the chitosan groups (FIGS. 3-5). Particularly, the control groups had a significantly lower expression of OMP than the chitosan groups at day 9. The ratio of OMP relative to GAPDH in the control groups at day 9 was 0.3±0.17, in contrast to 0.8±0.18 in the chitosan groups, exhibiting a significant difference (FIG. 5, $p<0.05$). The finding indicated that chitosan promoted the maturation of ORNs during this period.

<Expressions of Signal Transduction Apparatus of Rat ORNs>

Figure 6:
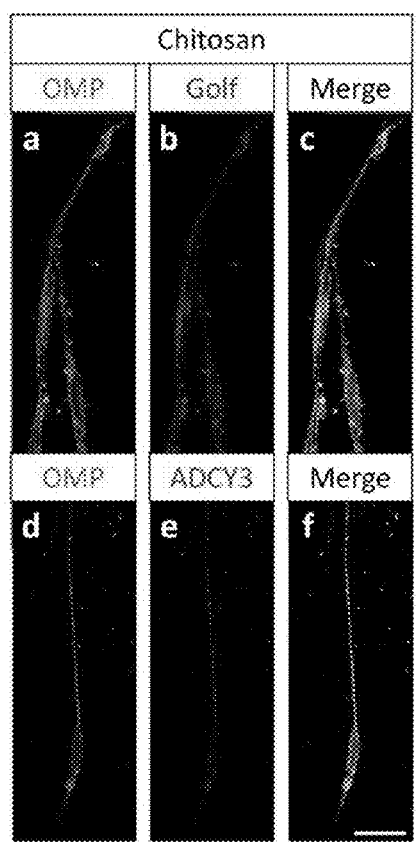
FIG. 6 shows immunofluorescence images of rat ONCs in control groups and chitosan-treated groups (with 0.1 mg/ml chitosan) at day 9 labeled by OMP (identified with green Dylight488), $G_{olf}$ (identified with red Alexa Fluor 555), ADCY3 (identified with red Alexa Fluor 555) (scale bar=20 μm)
Figure 7:
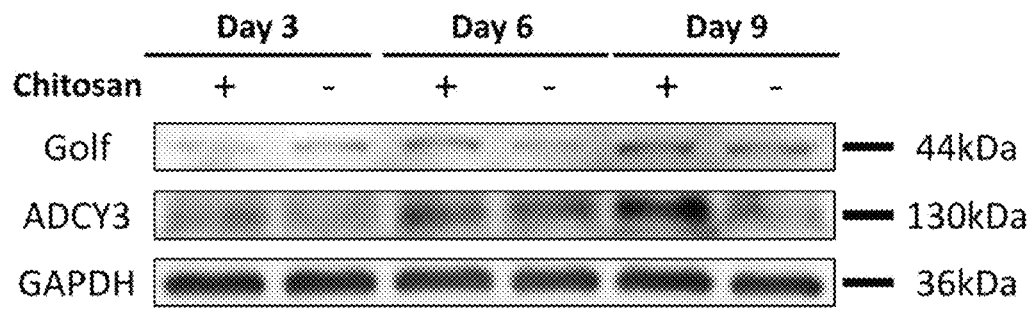
FIG. 7 shows the Western blot analysis for $G_{olf}$ and ADCY of rat ONCs in control groups and chitosan-treated groups (with 0.1 mg/ml chitosan) from day 3 to day 9.
Figure 8:
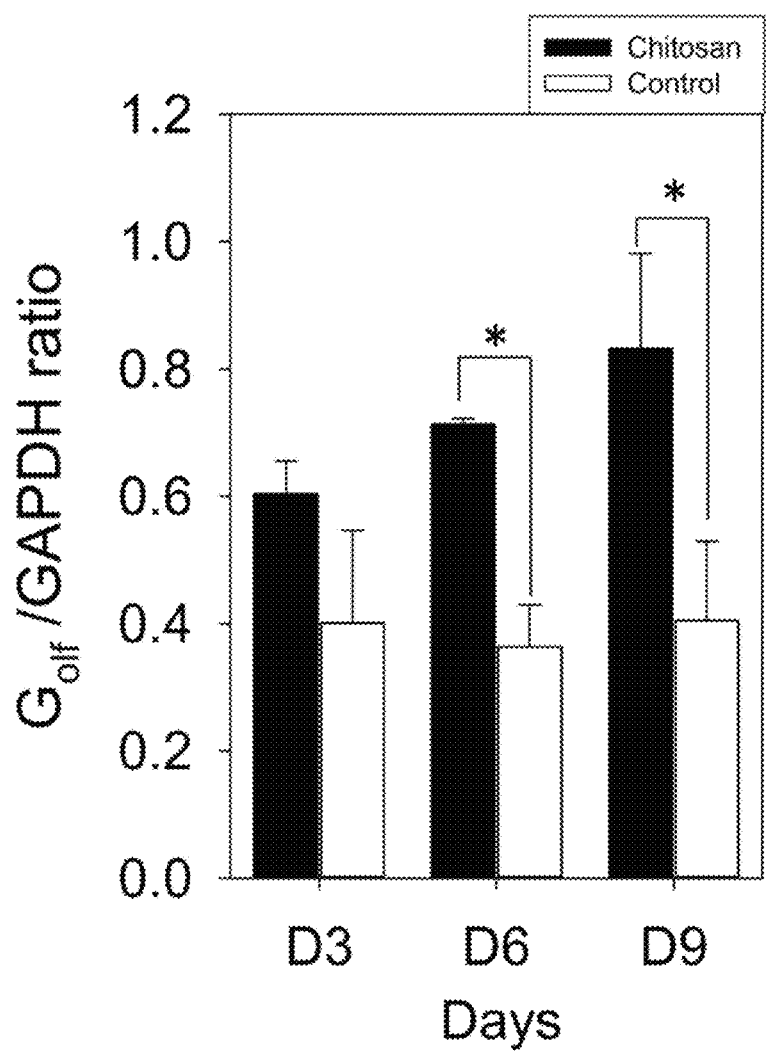
FIG. 8 shows the semi-quantitative analysis of Western blot for $G_{olf}$/GAPDH of rat ONCs in control groups and chitosan-treated groups (with 0.1 mg/ml chitosan) from day 3 to day 9, in which bar charts show mean±SD of five samples; *$p<0.05$.
Figure 9:
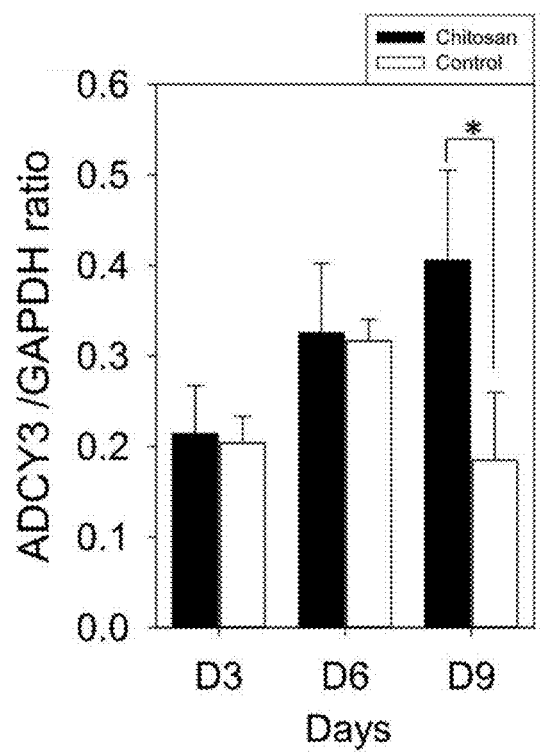
FIG. 9 shows the semi-quantitative analysis of Western blot for ADCY3/GAPDH of rat ONCs in control groups and chitosan-treated groups (with 0.1 mg/ml chitosan) from day 3 to day 9, in which bar charts show mean±SD of five samples; *$p<0.05$.

$G_{olf}$ and ADCY3 are essential components of signal transduction pathway for odorant receptors and neurotransmitter response. Results of immunostaining analysis showed that OMP-positive cells culture with chitosan also expressed $G_{olf}$ and ADCY3 (FIG. 6). $G_{olf}$ and ADCY3 were found throughout their cell bodies and membranes, respectively. Western blot analysis of $G_{olf}$ and ADCY3 further confirmed the results (FIGS. 7-9), and suggested that ORNs treated with chitosan expressed more signal transduction apparatuses than ORNs without treatment at day 9 ($p<0.05$). Therefore, chitosan-treated ONCs not only differentiated into ORNs but also enhanced their signal transduction apparatuses.

The above results demonstrate that the water-soluble chitosan can promote ONCs to differentiate into mature and functional ORNs. Since chitosan comprises a combination of D-glucosamine and N-acetyl-glucosamine, and the olfactory neuroepithelium is rich in numerous glycoconjugates, chitosan may interact with glycoconjugates to promote regeneration of the functional olfactory neuroepithelium. Additionally, chitosan can interact with mucin and adhere to nasal mucosa, and therefore may prolong the efficacy of treatment and be appropriate for intranasal topical administration. Likewise, chitosan oligosaccharide or any other water-soluble chitosan derivatives also can exhibit the aforementioned effects.

<Effects of Chitosan in Different Concentrations on Rat ONCs>

Figure 10:
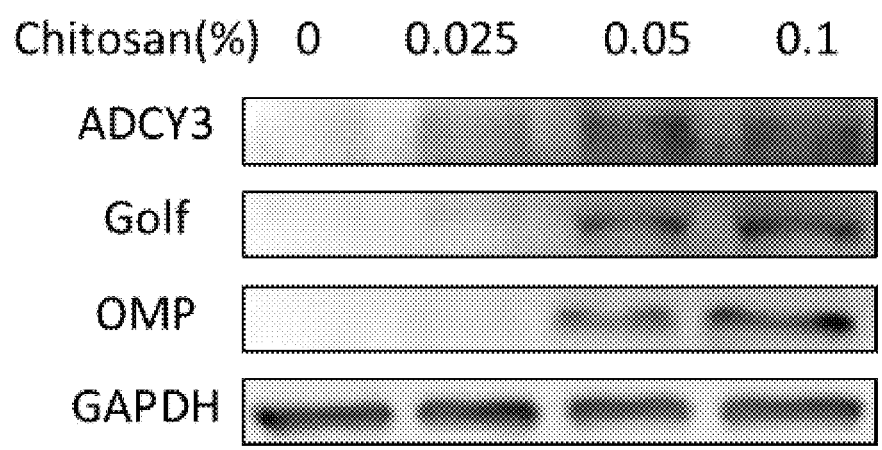
FIG. 10 shows the Western blot analysis for OMP, $G_{olf}$ and ADCY3 of rat ONCs in control groups and chitosan-treated groups (with 0.025%, 0.05%, 0.1% chitosan) at day 9.

Rat ONCs were cultured with the medium containing 0.025 wt %, 0.05 wt % and 0.1 wt % chitosan, respectively. The expression levels of OMP, $G_{olf}$ and ADCY3 were analyzed at day 9. The analysis revealed that higher-dose chitosan induced higher expression levels of OMP, $G_{olf}$ and ADCY3 (FIG. 10).

<Effects of Proteoglycans and Glycosaminoglycans on Rat ONCs>

Figure 11:
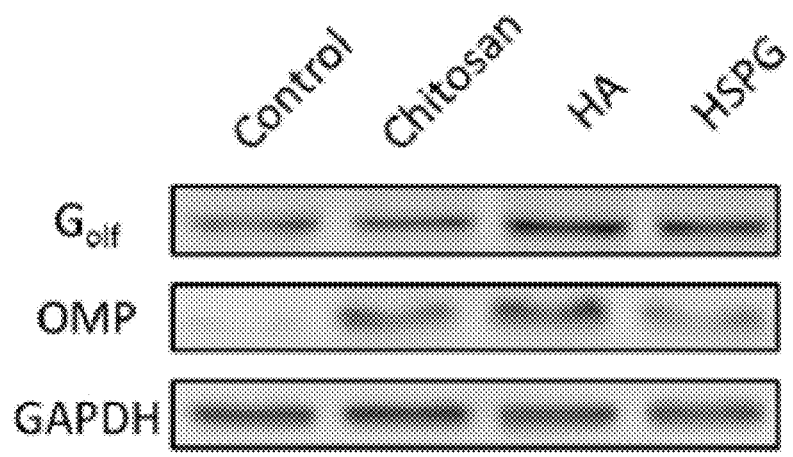
FIG. 11 shows the Western blot analysis for OMP and $G_{olf}$ of rat ONCs in control groups and administration groups (with 0.1 mg/ml chitosan, HA, HSPG) at day 9.
Figure 12:
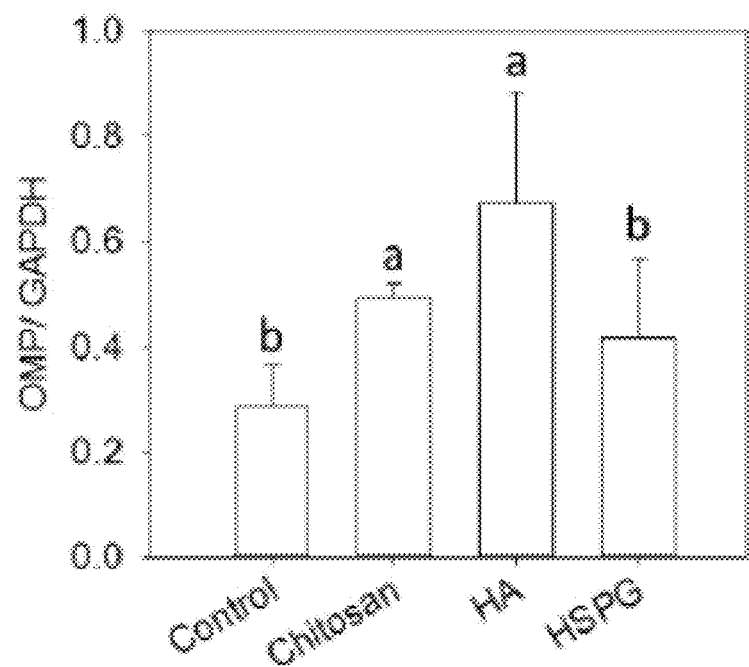
FIG. 12 shows the semi-quantitative analysis of Western blot for OMP/GAPDH of rat ONCs in control groups and administration groups (with 0.1 mg/ml chitosan, HA, HSPG) at day 9, in which bar charts show mean±SD of three samples; different letters means $p<0.05$.
Figure 13:
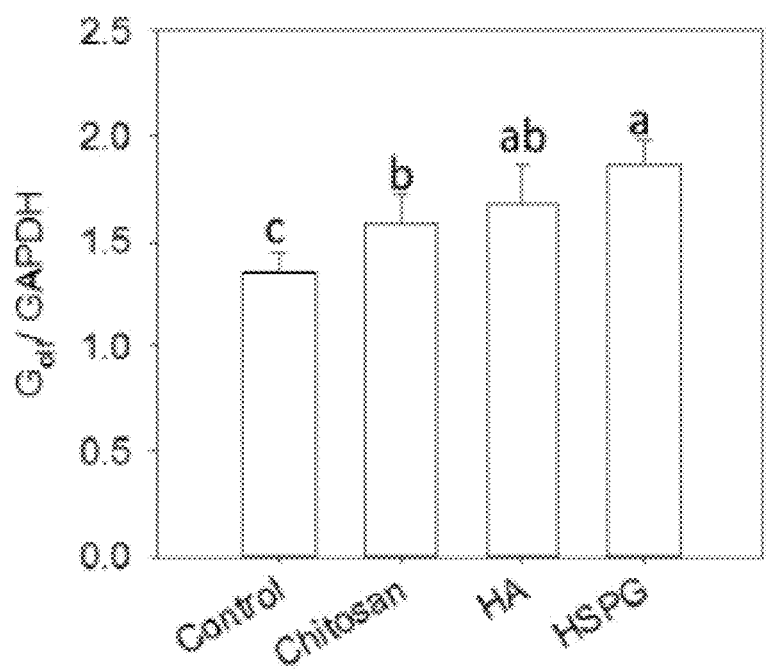
FIG. 13 shows the semi-quantitative analysis of Western blot for $G_{olf}$/GAPDH of rat ONCs in control groups and administration groups (with 0.1 mg/ml chitosan, HA, HSPG) at day 9, in which bar charts show mean±SD of three samples; different letters means $p<0.05$.

Rat ONCs were cultured with the medium containing 0.1 mg/ml chitosan, HA (HA200K-1, Lifecore biomedical, MN) and HSPG (H7640, Sigma-Aldrich, St. Louis, Mo.), respectively. The expression levels of OMP and $G_{olf}$ were analyzed at day 9. The analysis revealed that HA and HSPG promoted expression of mature and functional ORNs (FIGS. 11-13).

<Effects of Monosaccharide Monomers on Rat ONCs>

Figure 14:
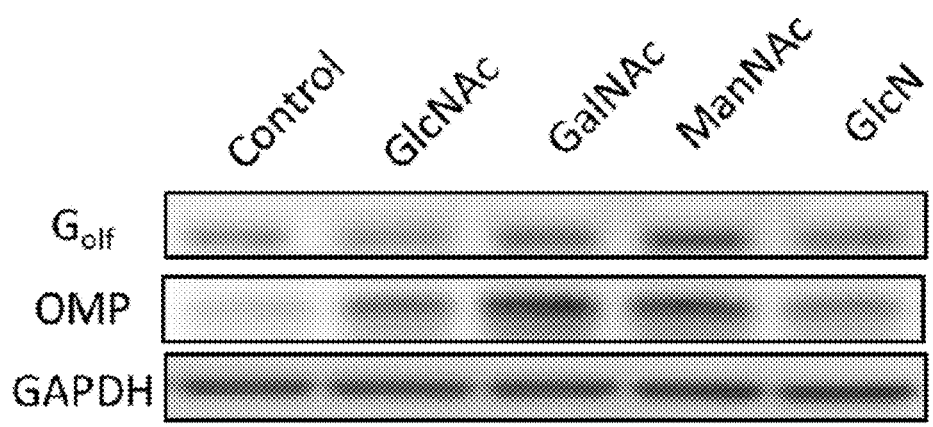
FIG. 14 shows the Western blot analysis for OMP and $G_{olf}$ of rat ONCs in control groups and administration groups (with 0.1 mg/ml GlcNAc, GalNAc, ManNAc, GlcN) at day 9.
Figure 15:
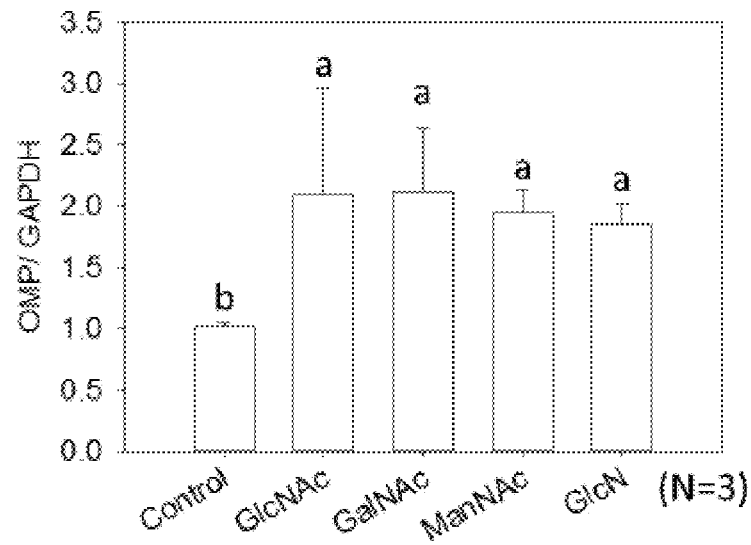
FIG. 15 shows the semi-quantitative analysis of Western blot for OMP/GAPDH of rat ONCs in control groups and administration groups (with 0.1 mg/ml GlcNAc, GalNAc, ManNAc, GlcN) at day 9, in which bar charts show mean±SD of three samples; different letters means p<0.05.
Figure 16:
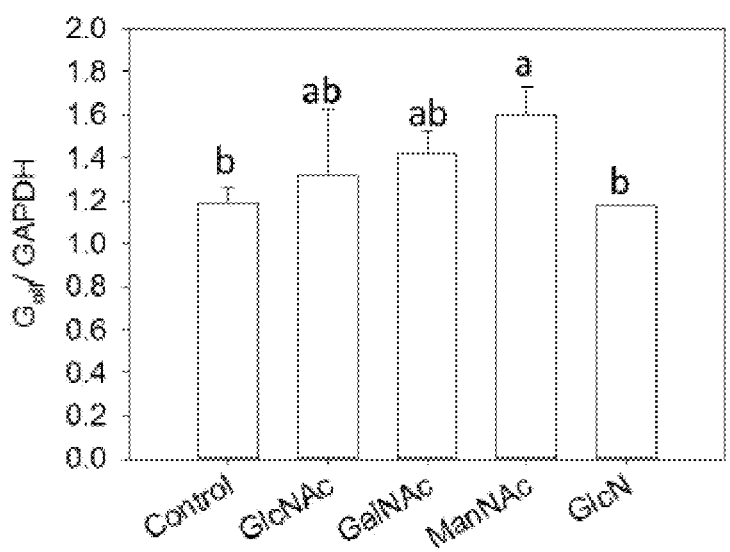
FIG. 16 shows the semi-quantitative analysis of Western blot for $G_{olf}$/GAPDH of rat ONCs in control groups and administration groups (with 0.1 mg/ml GlcNAc, GalNAc, ManNAc, GlcN) at day 9, in which bar charts show mean±SD of three samples; different letters means p<0.05.

Rat ONCs were cultured with the medium containing 0.1 mg/ml GlcNAc, GalNAc, ManNAc and GlcN, respectively. The expression levels of OMP and $G_{olf}$ were analyzed at day 9. The analysis revealed that these monomers of glycosaminoglycan promoted the maturation of ORNs (FIGS. 14-16).

<Effects of Chitosan on Human ONCs>

Figure 17:
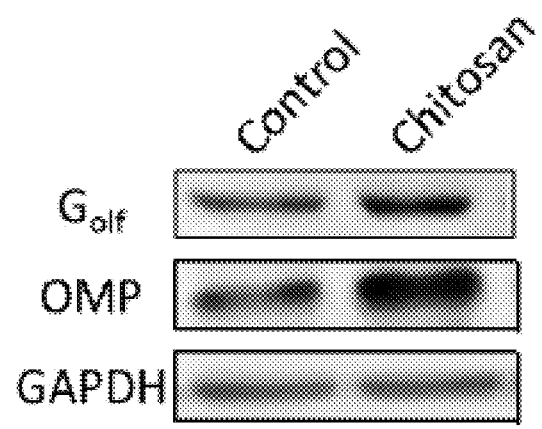
FIG. 17 shows the Western blot analysis for OMP and $G_{olf}$ of human ONCs in control groups and chitosan-treated groups (with 0.1 mg/ml chitosan) at day 9.
Figure 18:
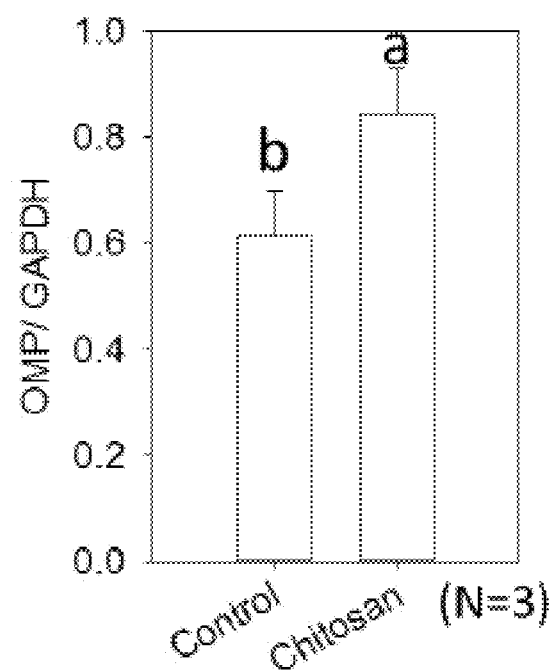
FIG. 18 shows the semi-quantitative analysis of Western blot for OMP/GAPDH of human ONCs in control groups and chitosan-treated groups (with 0.1 mg/ml chitosan) at day 9, in which bar charts show mean±SD of three samples; different letters means p<0.05.
Figure 19:
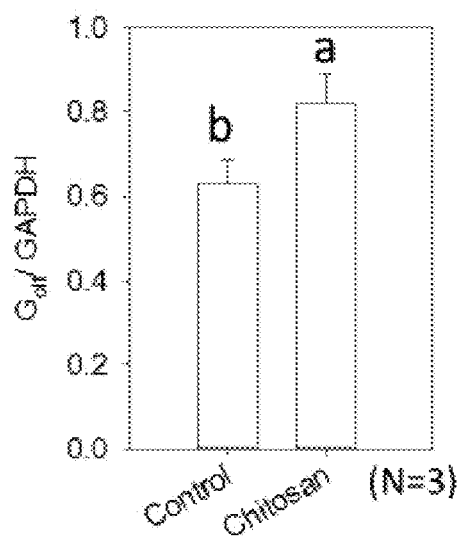
FIG. 19 shows the semi-quantitative analysis of Western blot for $G_{olf}$/GAPDH of human ONCs in control groups and chitosan-treated groups (with 0.1 mg/ml chitosan) at day 9, in which bar charts show mean±SD of three samples; different letters means p<0.05.

Human ONCs were cultured with the medium containing 0.1 mg/ml chitosan, and the expression levels of OMP and $G_{olf}$ were analyzed at day 9. The analysis revealed that chitosan induced positive effects on human ONCs (FIGS. 17-19).

<Effects of Monosaccharide Monomers on Human ONCs>

Figure 20:
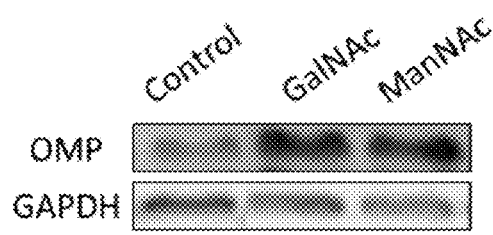
FIG. 20 shows the Western blot analysis for OMP of human ONCs in control groups and administration groups (with 0.1 mg/ml GalNAc, ManNAc) at day 9.

Human ONCs were cultured with the medium containing 0.1 mg/ml GalNAc and ManNAc, respectively, and the expression levels of OMP were analyzed at day 9. The analysis revealed that the monomers of glycosaminoglycans induced positive effects on human ONCs (FIG. 20).

<Effects of Chitosan Plus Glycosaminoglycans on Human ONCs>

Figure 21:
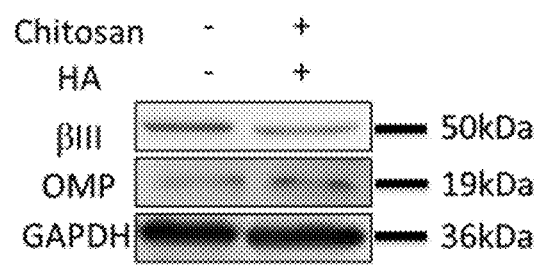
FIG. 21 shows the Western blot analysis for βIII tubulin and OMP of human ONCs in control groups and administration groups (with 0.1 mg/ml chitosan plus 2 mg/ml HA) at day 9.

Human ONCs were cultured with the medium containing 0.1 mg/ml chitosan and 2 mg/ml HA, and the expression levels of βIII tubulin and OMP were analyzed at day 9. The analysis revealed that the combination of chitosan and HA can promote the maturation of ORNs (FIG. 21).

<Effects of Chitosan Plus Neuropeptide Y on Human ONCs>

Figure 22:
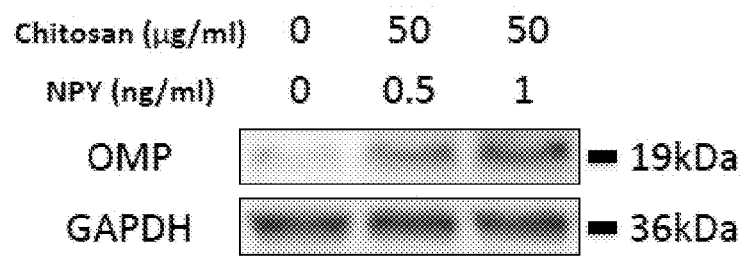
FIG. 22 shows the Western blot analysis for OMP of human ONCs in control groups and administration groups (with 50 μg/ml chitosan plus 0.5 ng/ml or 1 ng/ml neuropeptide Y) at day 9.
Figure 23:
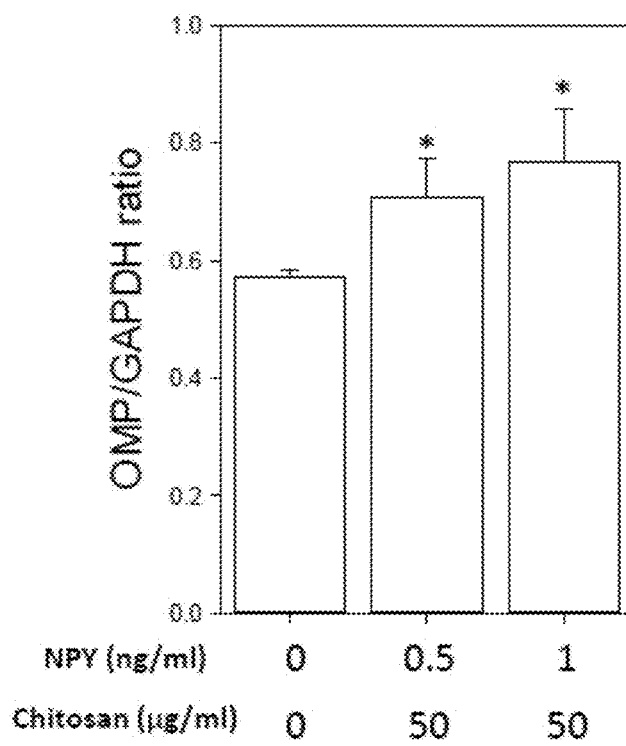
FIG. 23 shows the semi-quantitative analysis of Western blot for OMP/GAPDH of human ONCs in control groups and administration groups (with 50 ug/ml chitosan plus 0.5 ng/ml or 1 ng/ml neuropeptide Y) at day 9, in which bar charts show mean±SD of three samples; *p<0.05

Human ONCs were cultured with the medium containing 50 μg/ml (about 0.005 wt %) chitosan plus 0.5 ng/ml (about $5\times10^{-8}$ wt %) neuropeptide Y (NPY) and 50 μg/ml (about 0.005 wt %) chitosan plus 1 ng/ml (about $10\times10^{-8}$ wt %) neuropeptide Y, respectively. The expression levels of OMP were analyzed at day 9. The analysis revealed that the combination of chitosan and neuropeptide Y can promote the maturation of ORNs (FIGS. 22-23).

<Effects of Chitosan Plus Glycosaminoglycans on Human RECs>

Figure 24:
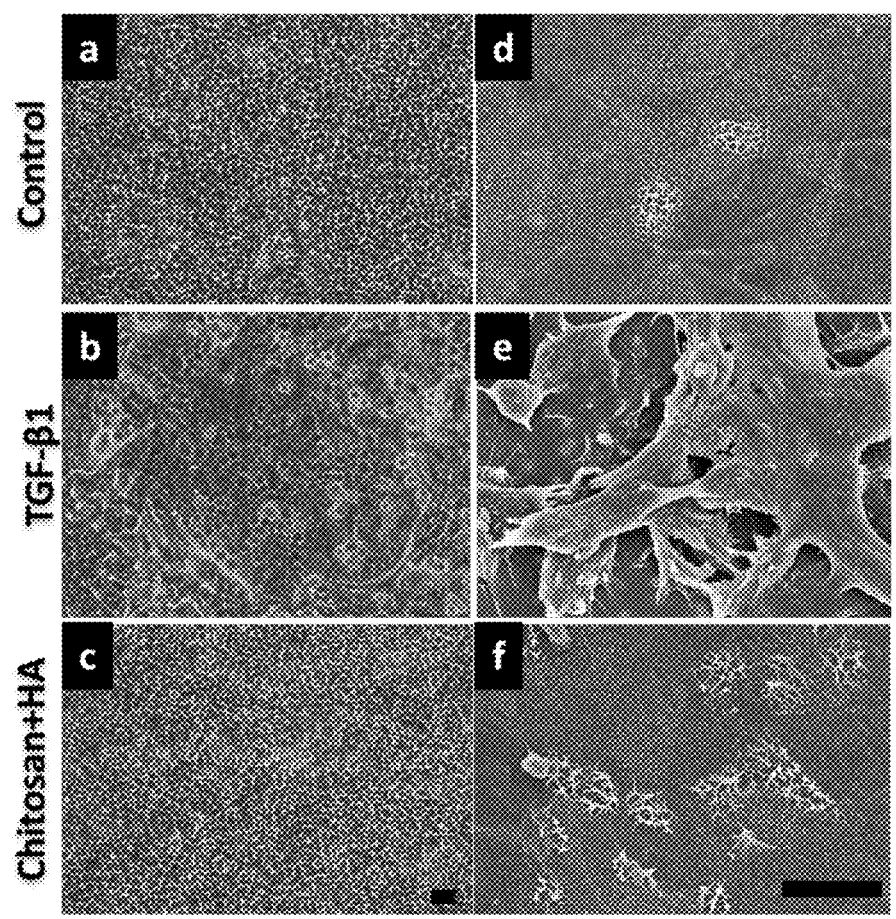
FIG. 24 shows the morphology of human RECs in control groups, comparison groups (with TGF-β1) and administration groups (with 0.1 mg/ml chitosan plus 2 mg/ml HA) at day 21 assessed by inverted (the left row) and scanning electron microscope (the right row) (Scale bar=20 μm)
Figure 25:
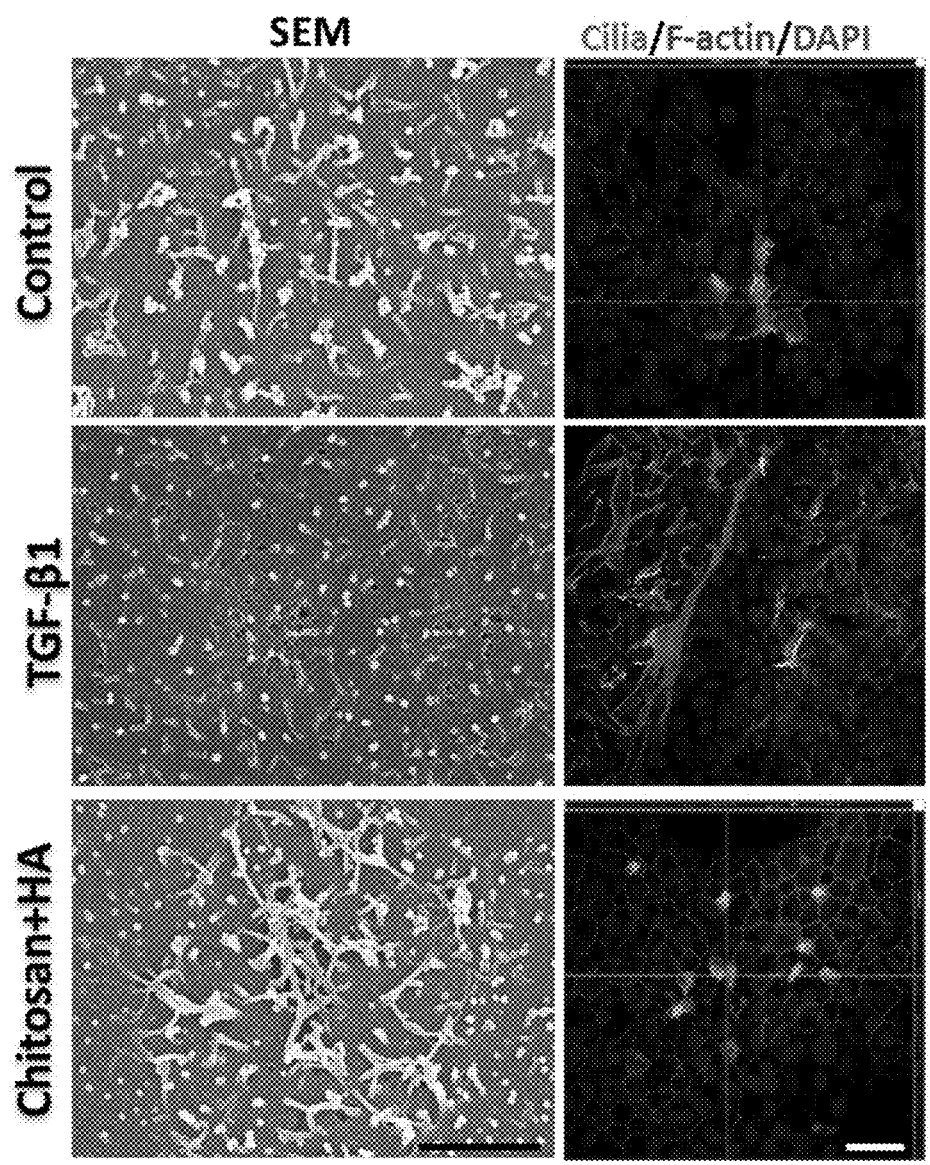
FIG. 25 shows the cilia morphology of human RECs in control groups (without chitosan), comparison groups (with TGF-β1) and administration groups (with 0.1 mg/ml chitosan plus 2 mg/ml HA) at day 21 assessed by scanning electron (the left row) (Scale bar=2 μm) and fluorescent microscope (the right row), in which cilia are identified with green Alexa 488 (Scale bar=20 μm)

In contrast to polygonal RECs observed in control groups, the RECs treated with TGF-β1 in comparison groups exhibited smooth cell boundary edges. However, after administration of 0.1 mg/ml chitosan plus 2 mg/ml HA, inflammation was inhibited and ciliogenesis (labeled with a ciliary marker, acetylated tubulin) and regeneration of RECs were promoted (FIGS. 24-25).

Animal Behavioral Analysis

<Rat Model of Anosmia>

21 male Sprague Dawley rats (seven-week-old) received an intraperitoneal (i.p.) injection of 300 mg/kg 3-methylindole (3-MI) dissolved in oil (100 mg/ml) to induce anosmia, and oil alone to 12 control (normal) rats. These 33 rats were sacrificed 3 rats according to time points (1, 2 and 3 weeks following soluble chitosan treatment). Finally, the olfactory neuroepithelium was obtained for immunohistochemistry and Western blot analyses.

<Chitosan Administration>

To prepare the chitosan solution, 10 mg/ml (about 1 wt %) soluble chitosan (Charming & beauty, Taiwan) was dissolved in sterilized PBS. Rats were anesthetized with inhaled isoflurane, and were dropped about 100 μl chitosan solution through nostrils after one week of 3-MI injection. The frequency of administration were twice a week until the indicated time points.

<Behavioral Tests>

Figure 26:
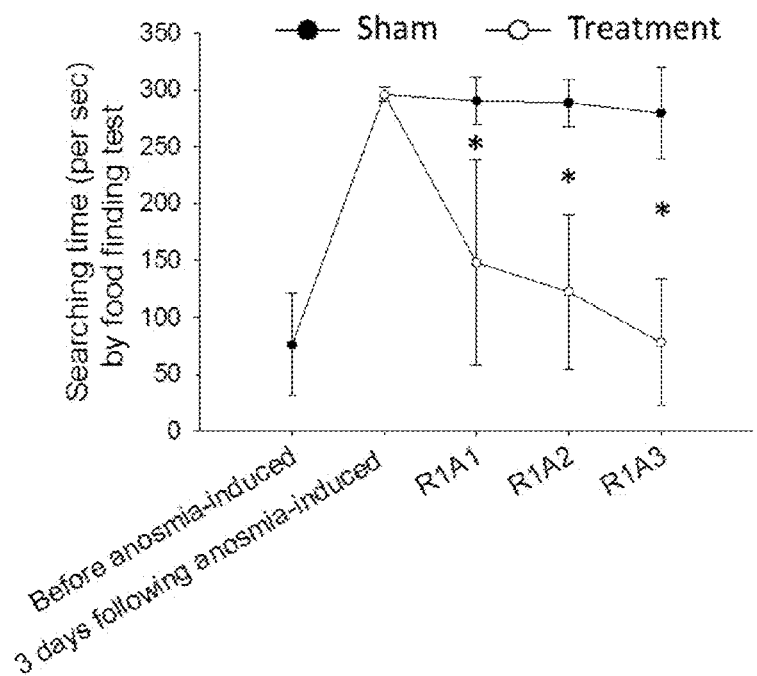
FIG. 26 shows the results of the rat behavioral test before and after 3-MI-induced anosmia, as well as after 1-, 2- and 3-week treatment with soluble chitosan, in which R1A1, R1A2 and R1A3 mean no treatment for 1 week after 3-MI-induced anosmia and then administration of 0.1 mg/ml chitosan for 1, 2 and 3 weeks, respectively; *p<0.05.

Olfactory function was assessed using a food-finding test in a T-maze. Briefly, the rats were restricted feeding for 3 days, and then released for 5 minutes in a T-maze where a food pellet was buried beneath wood shavings and randomly placed at the end of one of two horizontal arms. The food-finding test was repeated five times for each rat. The behavioral tests were performed before and after 3-MI-induced anosmia, as well as after 1-, 2- and 3-week treatment with soluble chitosan. It took about 80 seconds to find foods for the normal rats (before anosmia), but more than 300 seconds for 3 day anosmia-induced rats. After administration of chitosan for 3 weeks, the olfactory function of the anosmia-induced rats can be improved to normal level (before anosmia) (FIG. 26).

<Immunohistochemistry>

Figure 27:
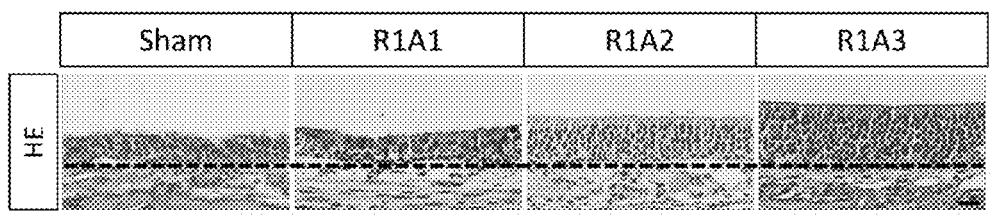
FIG. 27 shows the H&E staining results of rat olfactory neuroepithelium after 3-MI-induced anosmia, as well as after 1-, 2- and 3-week treatment with soluble chitosan, in which R1A1, R1A2 and R1A3 mean no treatment for 1 week after 3-MI-induced anosmia and then administration of 0.1 mg/ml chitosan for 1, 2 and 3 weeks, respectively; the dashed lines are taken as basis for measuring the thickness of olfactory neuroepithelium (Scale bar=20 μm)
Figure 28:
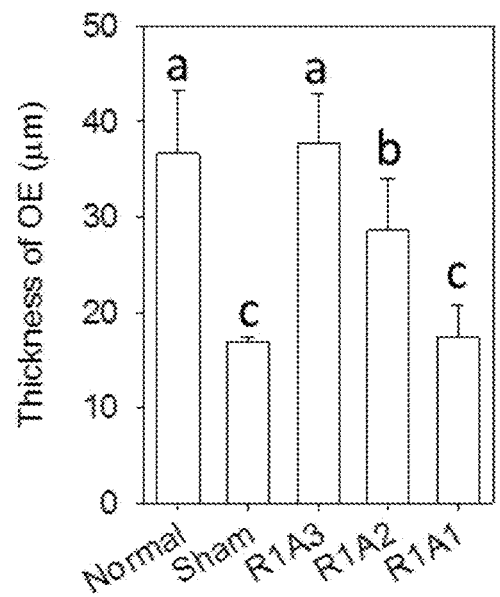
FIG. 28 shows the thickness of rat olfactory neuroepithelium before and after 3-MI-induced anosmia, as well as after 1-, 2- and 3-week treatment with soluble chitosan, in which R1A1, R1A2 and R1A3 mean no treatment for 1 week after 3-MI-induced anosmia and then administration of 0.1 mg/ml chitosan for 1, 2 and 3 weeks, respectively; bar charts show mean±SD of three samples; different letters means p<0.05.

For immunohistochemistry, one side of olfactory neuroepithelium was fixed in 10% paraformaldehyde at 4° C. overnight, decalcified, and embedded with paraffin. The sections of 4 μm thickness were performed hematoxylin and eosin (H&E) for evaluation of thickness of the olfactory neuroepithelium. The olfactory neuroepithelium was randomly captured by a digital microscope camera. The thickness of olfactory neuroepithelium was evaluated in the five corresponding areas of each rat. The results revealed that the thickness of olfactory neuroepithelium can be improved to normal level (before anosmia) by administration of chitosan for 3 weeks (FIGS. 27-28).

<Western Blot Analysis>

Figure 29:
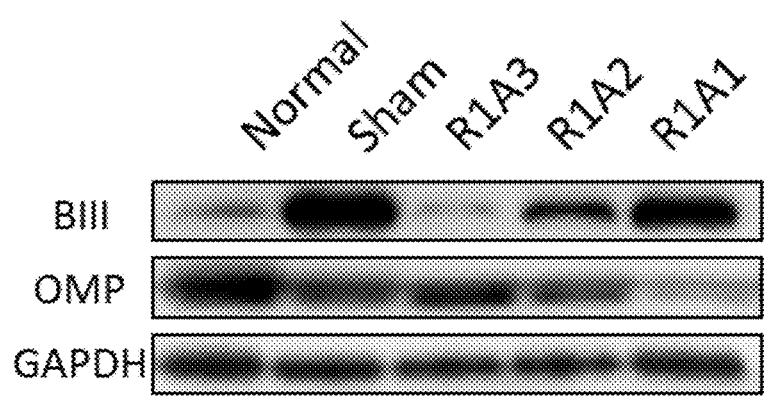
FIG. 29 shows the Western blot analysis for OMP andβIII tubulin of rat olfactory neuroepithelium before and after 3-MI-induced anosmia, as well as after 1-, 2- and 3-week treatment with soluble chitosan, in which R1A1, R1A2 and R1A3 mean no treatment for 1 week after 3-MI-induced anosmia and then administration of 0.1 mg/ml chitosan for 1, 2 and 3 weeks, respectively.
Figure 30:
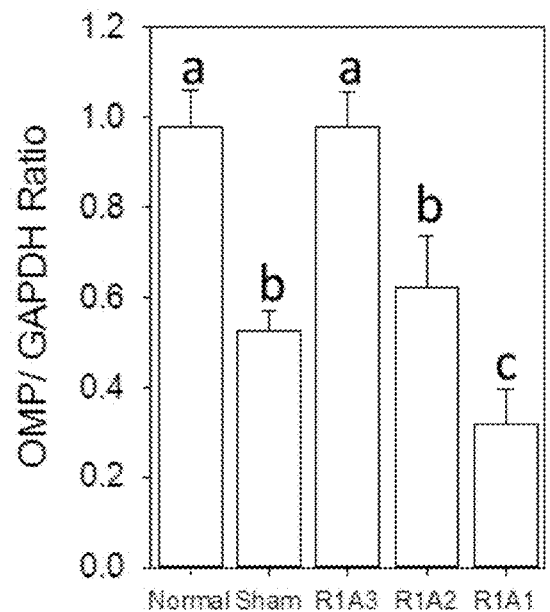
FIG. 30 shows the semi-quantitative analysis of Western blot for OMP/GAPDH of rat olfactory neuroepithelium before and after 3-MI-induced anosmia, as well as after 1-, 2- and 3-week treatment with soluble chitosan, in which R1A1, R1A2 and R1A3 mean no treatment for 1 week after 3-MI-induced anosmia and then administration of 0.1 mg/ml chitosan for 1, 2 and 3 weeks, respectively; bar charts show mean±SD of three samples; different letters means p<0.05.
Figure 31:
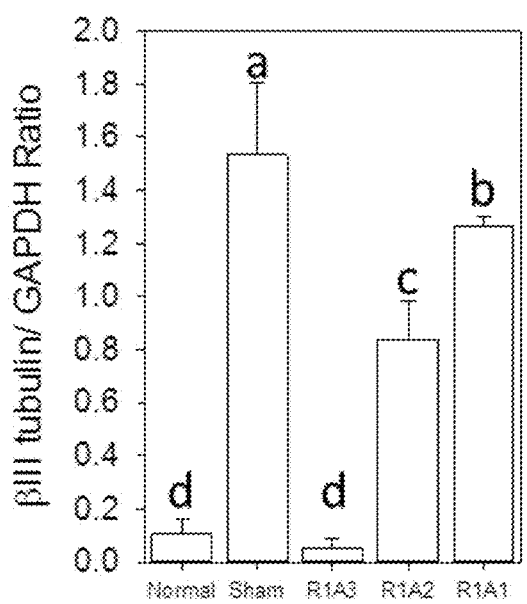
FIG. 31 shows the semi-quantitative analysis of Western blot for βIII tubulin/GAPDH of rat olfactory neuroepithelium before and after 3-MI-induced anosmia, as well as after 1-, 2- and 3-week treatment with soluble chitosan, in which R1A1, R1A2 and R1A3 mean no treatment for 1 week after 3-MI-induced anosmia and then administration of 0.1% chitosan for 1, 2 and 3 weeks, respectively; bar charts show mean±SD of three samples; different letters means p<0.05.

OMP is a representative marker of mature ORNs, while βIII tubulin is a widely accepted as indicating immature ORNs. After administration of 0.1 mg/ml chitosan, the maturation of ORNs was facilitated and the olfactory function reached the normal level (before anosmia) at the $3^{rd}$ week of treatment (FIGS. 29-31).

The above results confirmed that chitin-based substance, proteoglycans, glycosaminoglycans and monomers thereof can be used as an effective ingredient for treating olfactory dysfunction owing to their effects in facilitating regeneration of the olfactory neuroepithelium, differentiation of olfactory receptor neurons and expression of signal transduction apparatuses. Particularly, the animal experiments demonstrated that the olfactory function can be significantly improved by intranasal administration of the aforementioned saccharides twice per week for at least two weeks, and even reach normal level by 3-week continuous administration. Additionally, it was further confirmed that the aforementioned saccharides also facilitate regeneration of respiratory epithelium and mucociliary differentiation, and thus can be used as an effective ingredient for healthcare after surgical treatment of nasal diseases.

What is claimed is:

1. A method of improving olfactory function, which includes: administering an effective amount of saccharide to a subject suffering from olfactory disorder; and administering an effective amount of neuropeptide Y to the subject suffering from olfactory disorder, wherein the saccharide is a chitin-based material, proteoglycan, glycosaminoglycan, amino monosaccharide, N-acylated amino monosaccharide or a combination thereof.

2. The method of claim 1, wherein the chitin-based material is chitosan, chitosan oligosaccharide or water-soluble derivatives thereof.

3. The method of claim 1, wherein the proteoglycan is heparan sulfate proteoglycan.

4. The method of claim 1, wherein the glycosaminoglycan is hyaluronic acid.

5. The method of claim 1, wherein the amino monosaccharide is glucosamine.

6. The method of claim 1, wherein the N-acylated amino monosaccharide is N-acetylglucosamine, N-acetylgalactosamine, N-acetyl-D-mannosamine or a combination thereof.

7. The method of claim 1, wherein improving olfactory function comprises at least one of: facilitating regeneration of olfactory neuroepithelium, promoting differentiation of olfactory receptor neurons, and increasing expression of signal transduction apparatus.

8. The method of claim 7, wherein the signal transduction apparatus is olfactory neuron specific-G protein ($G_{olf}$), adenylate cyclase type 3 (ADCY3) or a combination thereof.

9. The method of claim 1, wherein the saccharide further induces at least one of: facilitating regeneration of respiratory epithelium, and promoting ciliogenesis.

10. The method of claim 9, wherein the saccharide is a combination of chitosan and hyaluronic acid.

11. The method of claim 1, wherein the saccharide is formulated into a solution form.

12. The method of claim 1, wherein the saccharide is included in a medicament by an amount of 0.001 wt % or more.

13. The method of claim 1, wherein the saccharide is delivered to the subject in need by intranasal topical administration.

14. The method of claim 1, wherein the saccharide is included in a medicament by an amount of 0.005 wt % or more, and the neuropeptide Y is included in the medicament by an amount of $5\times10^{-8}$ wt % or more.

* * * * *